United States Patent [19]

Trachtenberg

[11] Patent Number: 5,550,039

[45] Date of Patent: Aug. 27, 1996

[54] OLIGONUCLEOTIDE PRIMERS FOR HLA CLASS I B LOCUS DNA TYPING

[75] Inventor: Elizabeth A. Trachtenberg, Berkeley, Calif.

[73] Assignee: Hoffmann-La Roche Inc., Nutley, N.J.

[21] Appl. No.: 399,675

[22] Filed: Mar. 7, 1995

[51] Int. Cl.$^6$ ............................ C12P 19/34; C07H 21/04
[52] U.S. Cl. ............................ 435/91.2; 435/6; 435/810; 536/24.31; 536/24.33
[58] Field of Search ............................ 435/6, 91.2, 810; 536/24.31, 24.33

[56] References Cited

U.S. PATENT DOCUMENTS

| | | | |
|---|---|---|---|
| 4,683,195 | 7/1987 | Mullis et al. | 435/6 |
| 5,424,184 | 6/1995 | Santamaria et al. | 435/6 |

FOREIGN PATENT DOCUMENTS

| | | |
|---|---|---|
| 0540997 | 5/1993 | European Pat. Off. . |
| 9207956 | 5/1992 | WIPO . |
| 9219771 | 11/1992 | WIPO . |
| 9416713 | 8/1994 | WIPO . |
| 9421818 | 9/1994 | WIPO . |

OTHER PUBLICATIONS

Yoshida et al., *Human Immunol.* 34, 257–266 (1992).
Guttridge et al., *Tissue Antigens* 45, 213–215 (Mar. 1995).
Sadler et al., *Tissue Antigens* 44, 148–154 (Sept. 1994).
Olerup et al., *Tissue Antigens* 43, 253–256 (Apr. 1994).
Guttridge et al., *Tissue Antigens* 44, 43–46 (Jul. 1994).
Bunce et al., *Tissue Antigens* 45, 81–90 (Feb. 1995).
Dominguez et al., *Immunogentics* 36, 277–282 (1992).
Yao et al., *Human Immunol.* 42, 54–60 (1995).
Andrien et al., *Tissue Antigens* 42, 480–487 (1993).
Baxter–Lowe et al., Aug. 1989, "HLA Gene Amplification and Hybridization Analysis of Polymorphism" J. Clin. Invest. 84:613–618.
Bjorkman and Parham, 1990, "Structure, Function, and Diversity of Class I Major Histocompatibility Complex Molecules" Annu. Rev. Biochem. 59:253–288.
Ennis et al., Apr. 1990, "Rapid Cloning of HLA–A, B cDNA by Using the Polymerase Chain Reaction: Frequency and Nature of Errors Produced in Amplification" 87:2833–2837.

Hill et al., Mar. 1991, "HLA Class I Typing by PCR: HLA–B27 and an African B27 Subtype" Lancet 337:640–642.
Lawlor et al., Feb., 1991, "Ancient HLA Genes From 7,500—Year Old Archaeological Remains" Nature 249:785–788.
Zemmour and Parham, 1991, "HLA Class I Nucleotide Sequences, 1991" Immunogenetics 33:310–320.
Yoshida et al., 1992, "Polymerase–Chain–Reaction–Based Analysis of Polymorphism in the HLA–B Gene" Human Immunology 34:257–266.
Bodmer et al., 1994, "Nomenclature for Factors for the HLA System,1994" Tissue Antigens 44:1–18.
Bugawan et al., 1994, "A Method for Typing Polymorphism at the HLA–A Locus Using PCR Amplification and Immobilized Oligonucleotides Probes" Tissue Antigens 44:137–147.
Guttridge et al., 1994, "Identification of HLA–B35, B53, B18,B5, B78, and B17 Alleles by the Polymerase Chain Reaction Using Sequence–Specific Primers (PCR–SSP)" Tissue Antigens 44:43–46.
Hildebrand et al., 1994, "HLA–B15: A Widespread and Diverse Family of HLA–B Alleles" Tissue Antigens 43:209–218.
Olerup, 1994, "HLA–B27 Typing by a Group–Specific PCR Amplification" Tissue Antigens 43: 253–256.

*Primary Examiner*—Kenneth R. Horlick
*Attorney, Agent, or Firm*—George M. Gould; Stacey R. Sias; Douglas A. Petry

[57] ABSTRACT

The present invention provides primers for the polymerase chain reaction amplification of a nucleic acid sequence encompassing the polymorphic regions of the second, third, and fourth exons of the HLA Class I B gene (HLA-B). The polymorphic regions of the second, third, and fourth exons of the HLA-B gene contain sufficient variability so that each allele is uniquely identified by the nucleic acid sequence within these regions. The primers and amplification methods of the present invention enable genotyping at the HLA-B locus using samples from a variety of sources and for detecting allelic variants not distinguishable by serological methods. The HLA-B DNA genotyping can be used for tissue typing, determining individual identity, and identifying disease susceptible individuals.

21 Claims, No Drawings

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CTCCCACTCC ATGAGGTATT TC        22

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TTCGGCAGCC CCTCATGCTG T        21

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CACTCGAGCT CCCACTCCAT GAGGTATTTC        30

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CACTCGAGCC CACTCCATGA GGTATTTC        28

( 2 ) INFORMATION FOR SEQ ID NO:5:

( i ) SEQUENCE CHARACTERISTICS:
        ( A ) LENGTH: 29 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

CAGAGCTCTT CGGCAGCCCC TCATGCTGT 29

( 2 ) INFORMATION FOR SEQ ID NO:6:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

CAGAGCTCTC GGCAGCCCCT CATGCTGT 28

( 2 ) INFORMATION FOR SEQ ID NO:7:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

ACGTGGACGA CACNCNGTTC GTGA 24

( 2 ) INFORMATION FOR SEQ ID NO:8:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

CACTCGAGAC GTGGACGACA CNCNGTTCGT GA 32

( 2 ) INFORMATION FOR SEQ ID NO:9:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

CACTCGAGGT GGACGACACN CNGTTCGTGA 30

( 2 ) INFORMATION FOR SEQ ID NO:10:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

TGGGACCGGA ACACACAGAT CTT 23

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

TGGGACCGGG AGACACAGAT CTC 23

( 2 ) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CGGGAGACAC AGAAGTACAA GCG 23

( 2 ) INFORMATION FOR SEQ ID NO:13:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

TGGGACCGGA ACACACAGAT CTA 23

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TGGGACCGGA ACACACAGAT CTG 23

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GAGACACGGA ACATGAAGGC CTC 23

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GAGACACAGA TCTGCAAGGC CAAG     24

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TGGGACCGGN ANACACAGAT CTC     23

OLIGONUCLEOTIDE PRIMERS FOR HLA CLASS I B LOCUS DNA TYPING

This inventions was made with Government support under grant number HL47170-02 by e U.S. National Institutes of Health. Government has certain rights in the invention.

BACKGROUND OF THE INVENTION

1. Field of the Invention

The present invention relates to the field of molecular biology, immunogenetics, and nucleic acid chemistry. More specifically, it relates to methods and reagents for genotyping at the HLA Class I B locus. The invention therefore has applications in the field of medicine generally, and medical research and diagnostics specifically, the field of forensic science, and the field of molecular biology.

2. Description of Related Art

The major histocompatibility complex (MHC) includes a number of genes that encode glycoproteins that, together with the T cell receptor (TCR), are the key elements of specificity in the T cell response to foreign antigens. There are two structurally distinct, but related, families of MHC molecules that present antigens to two subsets of T cells: Class I MHC molecules present antigens to T cells that express the CD8 cell surface glycoprotein, and Class II MHC molecules present antigens to T cells that express the CD4 cell surface glycoprotein. See Bjorkman and Parham, 1990, *Ann. Rev. Biochem.* 59:253–288, incorporated herein by reference. For a general review of the HLA Class II genes and proteins, see Trowsdale et al., 1985, *Immunol. Rev.* 85:5; and Giles and Capra, 1985, *Adv. Immunol.* 37:1, both incorporated herein by reference.

The Class I gene products function as restriction elements in the presentation of mainly endogenous peptides to cytotoxic T lymphocytes and are the major barrier for allogeneic tissue transplantation. Accurate determination of allelic subtypes is essential for typing potential transplantation donors, where very precise HLA matching appears to be critical in minimizing risk of rejection or graft versus host disease.

Significant advances have been made in developing DNA based typing methods for determining the HLA Class H genotype of an individual. The polymerase chain reaction (PCR) is used to amplify a nucleic acid sequence encompassing polymorphic regions within the gene. Following amplification, the sequence variants present within the polymorphic regions are detected using sequence-specific oligonucleotide probes. For example, see Saiki et al., 1986, *Nature*, 324:163; Bugawan et al, 1988,*J. Immunol.* 141:4024–4030, Erlich and Bugawan, 1989, in: PCR Technology: Principles and Applications for DNA Amplification, ed. H. A. Erlich. Stockton Press, New York, N.Y.:193-208; Scharf et al., 1991, *Human Immunol.* 30:190–201; Erlich et al., 1991, *Eur. J. Immunogen.* 18:33–35, each incorporated herein by reference. Some of these DNA based typing methods are now commercially available for forensic, research and clinical use.

In contrast to the advances made in the field of HLA Class II DNA typing, little progress has been made in developing methods for HLA Class I DNA typing. One reason for this lack of progress is the complexity of the HLA Class I genes. The Class I includes the A, B, C, E, F, and G genes and the H, J, K, and L pseudogenes. The A, B, C, and E loci are known to each encode a large number of different alleles. The F and G loci are currently not believed to be polymorphic. The currently known differences are primarily in the second and third exons of these genes, although sequence variation in the fourth exon of these Class I genes is also known (see Zemmour and Parham, 1991, *Immunogenetics* 33:310–320, and Malissen et al., Feb. 1982, *Proc. Natl. Acad. Sci USA*79:893–897, both incorporated herein by reference).

SUMMARY OF THE INVENTION

The present invention provides amplification primers and methods useful for typing HLA Class I B Locus (HLA-B) nucleic acids. The invention enables the detection and identification of allelic variants, including variants not distinguishable by present serological, cellular, or biochemical methods. The present HLA-B typing methods facilitates typing tissue for transplantation, determining individual identity, and identifying disease susceptible individuals.

One aspect of the invention relates to oligonucleotide primers which enable the PCR amplification of a region of the HLA-B locus which encompasses the polymorphic regions of the second, third, and fourth exons. The HLA-B alleles can be identified by the nucleic acid sequence within these polymorphic regions. In a preferred typing method, the HLA-B alleles can be detected and identified following amplification by using sequence-specific probes which hybridize to the specific sequence variants which occur within these polymorphic regions.

The primers of the present invention hybridize to regions within the HLA-B locus which are conserved among the alleles and enable the amplification of the known HLA-B alleles. An important advantage of the primers of the present invention is that they not only enable amplification of all HLA-B alleles, but are specific to the HLA-B alleles, i.e., homologous sequences from other HLA genes and pseudogenes are not amplified. Because of the high degree of homology found among the HLA Class I genes and pseudogenes, amplification of nucleic acid from other HLA Class I genes and psuedogenes would interfere with HLA-B genotyping methods. The complexity and high degree of homology found among the HLA Class I genes and pseudogenes has, until now, prevented the specific amplification of all the HLA-B alleles. The amplification specificity provided by the primers of the present invention is an important and novel property which enables the simple and rapid genotyping of the HLA-B alleles.

Another aspect of the invention relates to group-specific oligonucleotide primers which enable the PCR amplification of a region of specific subsets of the HLA-B alleles.

Another aspect of the invention relates to methods for amplifying a region of the HLA-B locus which encompasses polymorphic regions of the second, third, and fourth exons. The methods comprise carrying out a polymerase chain reaction (PCR) using the HLA-B-specific amplification primers of the present invention.

Another aspect of the invention relates to kits which contain the amplification primers of the present invention. These kits can include additional reagents for genotyping at the HLA-B locus, such as a panel of sequence-specific probes sufficient to determine the HLA-B genotype. The kits can also comprise one or more amplification reagents, e.g., polymerase, buffers, and nucleoside triphosphates.

DETAILED DESCRIPTION OF THE INVENTION

To aid in understanding the invention, several terms are defined below.

The terms "HLA-B gene" and "HLA-B locus" refer to a transcribed region of DNA that contains the coding sequence for the HLA Class I B protein and the untranslated intervening sequences.

The term "alleles" refers to variants of the nucleotide sequence of a gene. An allele may be defined by the sequences within a region of the gene which may not include the entire gene. Hence, an allele may consist of a set of sequence variants, all of which contain the specific sequence within the region that defines the allele. For example, alleles in the present invention are identified by the nucleotide sequence within the amplified region, which includes exons 2, 3, and 4. Gene sequences which differ only outside of this region are not distinguished.

The term "genotype" refers to a description of the alleles of a gene contained in an individual or a sample.

The terms "polymorphic" and "polymorphism", as used herein, refer to the condition in which two or more variants of a specific DNA sequence can be found in a population.

The terms "polymorphic gene" and "polymorphic region" refer to that region of the DNA where a polymorphism occurs. A polymorphic region is referred to synonymously as a variable region.

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pydmidine base, or modified purine or pyrimidine base. Them is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA.

The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods is provided in Goodchild, 1990, *Bioconjugate Chemistry* 1(3): 165–187, incorporated herein by reference.

The term "hybridization" refers the formation of a duplex structure by two single stranded nucleic acids due to complementary base pairing. Hybridization can occur between fully complementary nucleic acid strands or between nucleic acid strands that contain minor regions of mismatch. Conditions under which only fully complementary nucleic acid strands will hybridize are referred to as "stringent hybridization conditions" or "sequence-specific hybridization conditions". Two single-stranded nucleic acids that are complementary except for minor regions of mismatch are referred to as "substantially complementary". Stable duplexes of substantially complementary sequences can be achieved under less stringent hybridization conditions. Those skilled in the art of nucleic acid technology can determine duplex stability empirically or can estimate duplex stability considering a number of variables including, for example, the concentration of the oligonucleotides, the length and base composition of the oligonucleotides, ionic strength, temperature, and incidence of mismatched base pairs.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template nucleic acid, but must be sufficiently complementary to hybridize with the template. Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product. The region of the primer which is sufficiently complementary to the template to hybridize is referred to herein as the hybridizing region.

As used herein, the "upstream" primer refers to the primer whose extension product is a subsequence of the coding strand of the HLA-B allele. The "downstream" primer refers to the primer whose extension product is a subsequence of the complementary non-coding strand.

The term "probe", as used herein, refers to a oligonucleotide which forms a duplex structure with a sequence of a target nucleic acid due to complementary base pairing. Probes are for detection or capture of the target nucleic acid. The probe will consist of or contain a "hybridizing region" consisting preferably of from 10 to 50 nucleotides, more preferably from 15 to 30 nucleotides, corresponding to a region of the target sequence. "Corresponding" means identical to or complementary to the designated nucleic acid. A probe oligonucleotide can contain or be bound to additional features which allow for the detection or immobilization of the probe but do not significantly alter the hybridization characteristics of the hybridizing region. For example, probes may be labeled by the incorporation of radiolabeled nucleotides or by being bound to a separate detectable moiety.

The terms "sequence-specific", "sequence-specific oligonucleotide", and "SSO" refer to an oligonucleotide wherein the hybridizing region is exactly complementary to a target sequence, and for which conditions exist such that the oligonucleotide will hybridize to, and only to, an exactly complementary sequence. Both primers and probes may be sequence-specific. The use of sequence-specific probes under sequence-specific (stringent) hybridization conditions enables the detection of a specific target sequence. Similarly, the use of sequence-specific primers under sequence-specific amplification conditions enables the specific amplification of those target sequences which contain the exactly complementary primer binding sites. Sequence-specific primers and probes contain a hybridizing region which is typically between 15 and 25 nucleotides in length, although somewhat longer or shorter hybridizing regions can be used depending on the composition and nucleotide sequence.

Sequence-specific or stringent hybridization conditions are well known in the art (see, e.g., Sambrook et al., 1985, *Molecular Cloning—A Laboratory Manual*. Cold Spring Harbor Laboratory, Cold Spring Harbor, N.Y., incorporated herein by reference). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridization conditions will allow sequence mismatches to be tolerated; the degree of mismatch tolerated can be controlled by suitable adjustment of the hybridization conditions.

The terms "target region"and "target nucleic acid" refers to a region of a nucleic acid which is to be amplified, detected, or otherwise analyzed. In the present invention, the target region usually includes a polymorphic region. The sequence to which a sequence-specific primer or probe is exactly complementary can be referred to as a "target sequence".

The term "thermostable polymerase enzyme" refers to an enzyme that is relatively stable to heat and catalyzes the polymerization of nucleoside triphosphates to form primer extension products that are complementary to one of the nucleic acid strands of the target sequence. The enzyme initiates synthesis at the 3' end of the primer and proceeds in the direction toward the 5' end of the template until synthesis terminates. A purified thermostable polymerase enzyme is described more fully in U.S. Pat. No. 4,889,818, incorporated herein by reference, and is commercially available from Perkin-Elmer, Norwalk, Conn.

The term "subsequence" as used herein, refers to a sequence which is contained within a second sequence. As defined and used herein, subsequence is intended to include within its scope the full-length sequence. Thus, for example, SEQ ID NO: 1 is included in the set of subsequences of SEQ ID NO: 1.

Conventional techniques of molecular biology and nucleic acid chemistry, which are within the skill of the art, are fully explained fully in the literature. See, for example, Sambrook et al., 1985, *Molecular Cloning—A Laboratory Manual*, Cold Spring Harbor Laboratory, Cold Spring Harbor, N.Y.; *Oligonucleotide Synthesis* (M. J. Gait, ed., 1984); *Nucleic Acid Hybridization* (B. D. Hames and S. J. Higgins. eds., 1984); and a series, *Methods in Enzymology* (Academic Press, Inc.), all of which are incorporated herein by reference. All patents, patent applications, and publications mentioned herein, both supra and infra, are incorporated herein by reference.

HLA-B Amplification Primers

The upstream primers of the present invention contain a hybridizing region which is a subsequence of SEQ ID NO:1 comprising nucleotides 5-21 of SEQ ID NO: 1. The downstream primers of the present invention contain a hybridizing region which is a subsequence of SEQ ID NO:2 comprising nucleotides 5-21 of SEQ ID NO: 2. The numbering of the nucleotides refers to the sequences oriented 5' to 3', as in tables, below. SEQ ID NO:1 is a 22 base sequence which hybridizes to the HLA-B alleles in the second exon from the third base of codon 1 through codon 8. SEQ ID NO:2 is a 21 base sequence which hybridizes to the HLA-B alleles in the fourth exon from third base of codon 78 through the second base of codon 85. The region flanked by the primers, codon 8 of the second exon through codon 78 of the fourth exon, encompasses the polymorphic regions within the HLA-B locus. The sequences of the primer hybridizing regions are provided in Table 1, below, with the minimum subsequences useful as primer hybridizing regions shown in bold.

TABLE 1

| HLA-B Amplification Primer Hybridizing Regions | | |
|---|---|---|
| Upstream Primer | SEQ ID NO: 1 | 5'-CTCCCACTCCATGAGGTATTTC |
| Downstream Primer | SEQ ID NO: 2 | 5'- TTCGGCAGCCCCTCATGCTGT |

The hybridization specificity of the primers is a critical property of the primers which enables the amplification of the known HLA-B alleles without the simultaneous amplification of homologous sequences from other Class I genes and pseudogenes. Because the hybridization specificity of a primer depends on the exact length and base composition of the hybridizing region, only minor modifications can be made to a primer hybridizing sequence without adversely affecting the utility of the primers. The above description of the primer hybridizing regions in terms of subsequences of SEQ ID NO:1 and SEQ ID NO:2 reflects the sequence modifications which can be made to the primer hybridizing regions while maintaining the function of the primers. In essence, the primer hybridizing regions must consist of SEQ ID NO:1 and SEQ ID NO:2 with minor deletions, however, being tolerated.

In general, the 3' end, which is the primer extension site, is more critical to the specificity of the primer. A single base deletion from the 3' end of the upstream primer hybridizing region, SEQ ID NO:1, can be made without significantly altering the specificity of the upstream primer. However, the 3' end of the downstream primer hybridizing region, SEQ ID NO:2, is critical and cannot be extended or deleted.

At the 5' end of each primer hybridization region, up to about 4 bases can be deleted without losing the HLA-B-specific hybridization properties. If desired, such minor deletions to the hybridizing region can be made in order to adjust the hybridization conditions under which the primer is used. The amplification conditions described in the examples am preferred for amplifications using the preferred primers whose hybridizing regions consist of SEQ ID NO:1 and SEQ ID NO:2, respectively. One of skill in the art will realize that the use of shorter primer sequences, which require a lower temperature to stably hybridize to the target sequence, would require modification of the amplification conditions.

In a preferred embodiment of the invention, the upstream primer consists of SEQ ID NO:1 extended with an additional sequence at the 5' end and the downstream primer consists of SEQ ID NO:2 extended with an additional sequences at the 5' end, wherein the additional 5' sequences contain restriction enzyme cleavage sites (restriction sites). The restriction sites, which are incorporated into the amplified product, facilitate cloning the amplified product for use in sequencing (see U.S. Pat. No. 4,683,195). Typically, sequences between about 2 and about 10 bases in length can be added to the 5' end of the primer hybridizing region without significantly altering of the ability of the primers to catalyze the specific amplification of HLA-B alleles. One of skill in the art will realize that minor optimization of the amplification conditions may be necessary depending on the sequence added.

The exact length and sequence of the added 5' terminal sequences will be determined by the restriction site desired. In general, particular restriction sites are chosen based on the restriction sites contained in a particular selected cloning vector. The amplified product can be cloned into a suitable vector, such as the Bluescript plasmid available from Stratagene (La Jolla, Calif.), using standard techniques (see Sambrook et al., supra). Techniques for sequencing the cloned amplification product are well-known in the an.

In a particularly preferred embodiment, amplification of the known HLA-B alleles is carded out using primers ET1148 (SEQ ID NO: 3) and ET1147 (SEQ ID NO: 5). The sequences of ET1148 (SEQ ID NO: 3)and ET1147 (SEQ ID NO:5)are provided in Table 2 along with similar primer containing 5' -truncated hybridizing regions. Upstream primer ET1148 (SEQ ID NO:3) contains an 8 base sequence which contains a Xho I restriction cleavage site added to the 5' end of SEQ ID NO:1. Downstream primer ET1147 (SEQ ID NO:5) contains an 8 base sequence which contains a Sac I restriction cleavage site added to the 5' end of SEQ ID NO:2. These primers amplify a 1636 base-pair (bp) fragment from the known HLA-B alleles. Amplification conditions for using ET1148 (SEQ ID NO: 3) and ET1147 (SEQ ID NO: 5) are described in the Examples.

TABLE 2

| Primer | Seq ID No. | HLA-B Amplification Primers Sequence |
| --- | --- | --- |
| ET1148 | 3 | 5'-CACTCGAGCTCCCACTCCATGAGGTATTTC |
| ET1129 | 4 | 5'-CACTCGAGCCCACTCCATGAGGTATTTC |
| ET1147 | 5 | 5'-CAGAGCTCTTCGGCAGCCCCTCATGCTGT |
| ET1130 | 6 | 5'-CAGAGCTCTCGGCAGCCCCTCATGCTGT |

Alternate HLA-B Amplification Primers

Alternate upstream primers which, together with ET1147 (SEQ ID NO: 5), amplify all HLA-B alleles with the exception of B *540 1 are provided in Table 3. These primers hybridize to codons 27-35 and, therefore, the first polymorphic region within the second exon is not available in the amplified product for genotyping. These primers amplify a 1564 bp fragment of the HLA-B alleles.

Primer ET1074 (SEQ ID NO: 7) consists of only a hybridizing region and does not contain an additional restriction enzyme cleavage site. Primers ET1145 (SEQ ID NO:8) and ET1146 (SEQ ID NO:9) contain an additional 8 base sequence which contains an Xho I restriction enzyme cleavage site. The hybridizing region of ET1146 is equivalent to ET1174 (SEQ ID NO:7) shortened at the 5' end by 2 bases. Between 0 and 4 bases can be deleted from the 5' end of the hybridizing region which is SEQ ID NO:7 without significantly altering the utility of the primer. Thus, the alternate HLA-B primers of the invention consists of a hybridizing region which is a subsequence of SEQ ID NO:7 comprising bases 5–24, and optionally a sequence at the 5' end between about 2 and about 10 bases in length which contains a restriction enzyme cleavage site.

In Table 3, "N" designates an inosine base.

TABLE 3

| Primer | Seq. ID No. | Alternate HLA-B Amplification Primers Sequence |
| --- | --- | --- |
| ET1074 | 7 | 5'-ACGTGGACGACACNCNGTTCGTGA |
| ET1145 | 8 | 5'-CACTCGAGACGTGGACGACACNCNGTTCGTGA |
| ET1146 | 9 | 5'-CACTCGAGGTGGACGACACNCNGTTCGTGA |

Group-Specific Primers

The present invention also provides group-specific primers which amplify a region of a subset of the HLA-B alleles. The HLA-B alleles can be divided into groups based on the variant sequence present within the polymorphic subregions within codons 60-70 of the second exon. Preferred group-specific primers are provided in Table 4, below. Each of the primers is used together with ET1147 (SEQ ID NO:5) to amplify the HLA-B alleles within the corresponding group.

The sequences provided in Table 4 are the hybridizing sequences and do not include additional sequences containing restriction enzyme cleavage sites. The group-specific primers of the present invention, in addition to the nucleotide sequences provided in Table 4, may include an additional sequence between about 2 and about 10 bases in length which at the 5' end which incorporates a restriction enzyme cleavage site. For example, the group-specific primers of the present invention may include the sequence 5'-CACTCGAG at the 5' end which incorporates an Xho I restriction enzyme cleavage site. Between 0 and 4 bases can be deleted from the 5' end of the hybridizing regions provided in Table 4 without significantly altering the utility of the primers. Thus, the group-specific HLA-B primers of the invention consist of a hybridizing region which is a subsequence of one of the primer sequences of Table 4 comprising bases 5 through the 3' terminal base, and optionally a sequence at the 5' end between about 2 and about 10 bases in length which contains a restriction enzyme cleavage site.

The Group 8-specific primer, ET1163 (SEQ ID NO:17), is a modification of ET1076 (SEQ ID NO:11) in which inosine replaces two bases. The presence of inosine allows ET1163 (SEQ ID NO:17) to amplify, in addition to the alleles of Group 2, alleles which differ only at codon 64 (i.e., Asn instead of Glu encoded by codon 64). Thus, as defined by the primers of Table 4, Group 2 is a subset of Group 8. In Table 4, "N" designates an inosine base.

TABLE 4

Group-Specific Primers

| Group | Primer | Seq. ID No. | Sequence |
|---|---|---|---|
| 1. | ET1075 | 10 | 5'-TGG GAC CGG AAC ACA CAG ATC TT |
| 2. | ET1076 | 11 | 5'-TGG GAC CGG GAG ACA CAG ATC TC |
| 3. | ET1077 | 12 | 5'-CGG GAG ACA CAG AAG TAC AAG CG |
| 4. | ET1078 | 13 | 5'-TGG GAC CGG AAC ACA CAG ATC TA |
| 5. | ET1079 | 14 | 5'-TGG GAC CGG AAC ACA CAG ATC TG |
| 6. | ET1080 | 15 | 5'-GAG ACA CGG AAC ATG AAG GCC TC |
| 7. | ET1081 | 16 | 5'-GAG ACA CAG ATC TGC AAG GCC AAG |
| 8. | ET1163 | 17 | 5'-TGG GAC CGG NAN ACA CAG ATC TC |

The alleles amplified using the group-specific primers together with ET1147 (SEQ D NO:5) are listed below in Table 5. Amplification conditions are described in the Examples. For convenience, the official allele designations specified by the WHO Nomenclature Committee (see Bodmer et al., 1991, *Tissue Antigens* 37:97–104, incorporated herein by reference) have been abbreviated by deletion of the "B*" prefix. For example, allele B*0801 is designated below as 0801.

TABLE 5

Allele Groups

| | |
|---|---|
| Group 1 alleles: | 0802, 1508, 3501, 3502, 3503, 3504, 3505, 3506, 3507, 3508, 5101, 5102, 5103, 5104, 5301, 7801 |
| Group 2 alleles: | 1301, 1302, 1501, 1503, 1504, 1505, 1506, 1507, 1512, 1514, 1519, 1520, 3701, 3902, 4001, 4002, 4003, 4004, 4005, 4006, 4101, 4401, 4402, 4403, 4404, 4501, 4701, 4801, 4802, 4901, 5001, 5201 |
| Group 3 alleles: | 4601 |
| Group 4 alleles: | 0702, 0703, 0704, 1511, 4201, 5401, 5501, 5502, 5601, 5602, 6701 |
| Group 5 alleles: | 1401, 1402, 1509, 1510, 1518, 3801, 3901, 3903, 7301 |
| Group 6 alleles: | 1516, 1517, 5701, 5702, 5801 |
| Group 7 alleles: | 2702, 2703, 2705, 2706, 2707, 2708 |
| Group 8 alleles: | Group 2 alleles plus 1502, 1513, 1515, 1801, and 1802 |

One use of group-specific primers is to resolve ambiguous allele identifications which can arise when amplifying nucleic acid from samples containing two alleles. Because alleles ate identified by the pattern of hybridization with a set of sequence-specific probes, ambiguity can arise while typing samples which contain two alleles even if the set of probes used can distinguish all HLA-B alleles in homozygous samples. The ambiguity arises because it may not be possible to determine to which allele in the sample each probe hybridized; only the combined pattern is observed. Amplification of a subset of the alleles using group-specific primers can resolve the ambiguity by selectively amplifying using a group-specific primer only one of the two possible alleles identified from the initial ambiguous identification. In this manner, the probe hybridization pattern following the second, group-specific, amplification indicates the sequence variants present in the single, amplified allele. The use of group-specific primers to resolve typing ambiguities is discussed in the product insert for the GeneAmplimer HLA DRB Allele-Specific Primer Set available from Perkin Elmer, Norwalk, Conn., incorporated herein by reference.

Amplification

The polymerase chain reaction (PCR) amplification process is well known in the art and described in U.S. Pat. Nos. 4,683,195; 4,683,202; and 4,965,188, each incorporated herein by reference, and in Saiki et al., 1988, *Science* 239:487; Scharf et al., 1988, *Hum. Immunol.* 22:61; and Scharf et al., 1989, *Proc. Natl. Acad. Sci. USA* 86:6215, each incorporated herein by reference. Commercial vendors, such as Perkin Elmer, Norwalk, Conn., market PCR reagents and publish PCR protocols. For ease of understanding the advantages provided by the present invention, a summary of PCR is provided.

In each cycle of a PCR amplification, a double-stranded target sequence is denatured, primers are annealed to each strand of the denatured target, and the primers are extended by the action of a DNA polymerase. The process is repeated typically between 25 and 40 times. The two primers anneal to opposite ends of the target nucleic acid sequence and in orientations such that the extension product of each primer is a complementary copy of the target sequence and, when separated from its complement, can hybridize to the other primer. Each cycle, if it were 100% efficient, would result in a doubling of the number of target sequences present.

In general, the nucleic acid in the sample will be DNA, most usually genomic DNA. However, the present invention can also be practiced with other nucleic acids, such as messenger RNA or cloned DNA, and the nucleic acid may be either single-stranded or double-stranded in the sample and still be suitable for purposes of the present invention. Those skilled in the art recognize that whatever the nature of the nucleic acid, the nucleic acid can be typed by the present method merely by taking appropriate steps at the relevant stage of the process. In general, regardless of the nature of the initial nucleic acid in the sample, the amplified products following PCR comprise double-stranded DNA.

Simple and rapid methods of preparing samples for PCR are described in Higuchi, 1989, in: PCR Technology: Principles and Applications for DNA Amplification, ed. H. A. Erlich. Stockton Press, New York, N.Y.:31-35. Any type of tissue containing HLA-B nucleic acid may be used for determining the HLA-B genotype of an individual; the methods are not limited to typing cells which express the HLA-B gene. Because the PCR technique can amplify extremely small quantities of nucleic acid, the HLA-B genotype can be determined from samples, such as single hairs, which contain a small number of target sequences. The feasibility of using single sperm for DNA typing is demonstrated in Li et al, 1988, *Nature* 335:441–417.

Due to the enormous amplification possible with the PCR process, small levels of DNA carryover from samples with high DNA levels, positive control templates, or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, *Nature*, 339:237-238 and Kwok, and Orrego, in: Innis et al. eds., 1990 *PCR Protocols: A Guide to Methods and Applications*, Academic Press, Inc., San Diego, Calif., which are incorporated herein by reference.

Enzymatic methods to reduce the problem of contamination of a PCR by the amplified nucleic acid from previous reactions are described in PCT patent publication U.S. Ser. No. 91/05210 and U.S. Pat. No. 5,035,996, both incorporated herein by reference. The methods allow the enzymatic degradation of any amplified DNA from previous reactions. PCR amplifications are carried out in the presence of dUTP instead of dTYP. The resulting double-stranded amplification product which incorporates uracil is subject to degradation by uracil-N-glycosylase (UNG), whereas normal thymine-containing DNA is not degraded by UNG. Amplification reaction mixture are treated with UNG before amplification to degrade all uracil containing DNA that could serve as target. Because the only source of uracil-containing DNA is the amplified product of a previous reaction, this method effectively eliminates the problem of contamination from previous reactions (carryover). UNG is rendered temporarily inactive by heat, so the denaturation steps in the amplification procedure also serve to inactivate the UNG. New amplification products, therefore, though incorporating uracil, are formed in an UNG-inactivated environment and are not degraded.

Amplification reaction mixtures are typically assembled at room temperature, well below the temperature needed to insure primer hybridization specificity. Non-specific amplification may result because at room temperature the primers may bind non-specifically to other, only partially complementary nucleic acid sequences, and initiate the synthesis of undesired nucleic acid sequences. These newly synthesized, undesired sequences can compete with the desired target sequence during the amplification reaction and can significantly decrease the amplification efficiency of the desired sequence. Non-specific amplification can be reduced using a "hot-start" protocol wherein one or more reagents me withheld from the reaction mixture until the temperature is raised sufficiently to provide the necessary hybridization specificity.

Preferred methods of educing non-specific amplification are described in copending U.S. Ser. No. 07/960,362, U.S. Pat. No. 5,418,149 which is incorporated herein by reference. The methods described therein reduce non-specific amplification by degrading any newly synthesized nucleic acid synthesized after the reaction mixture is assembled but prior to the start of the amplification reaction. By degrading any newly synthesized nucleic acid, no amplifiable nucleic acid target sequences resulting from primers hybridized to unintended sequences are present when the high temperature amplification reaction is carried out. The degradation of newly-synthesized nucleic acid is achieved by incorporating into the reaction mixture dUTP and UNG, and incubating the reaction mixture at 45°–60° C. prior to carrying out the amplification reaction.

Analysis of Amplified

Following amplification, the HLA allele present can be determined by analyzing the sequence of the amplified region. Sequence analysis is preferably carried out by hybridization with a set of sequence-specific oligonucleotide probes, although other methods, such as direct sequencing of the amplified nucleic acid, can be used.

Although the extensive sequence diversity of the HLA-B alleles is spread out over the second, third, and fourth exons, the variability within the second, third, and fourth exons of the HLA-B locus is largely confined to several discrete polymorphic, or variable, regions. The HLA-B alleles are uniquely identified by the sequence variants present within each of the variable regions. The sequence variants can be detected by hybridization with a set of sequence-specific probes, wherein each probe in the set hybridizes to a different variant sequence which occurs within one of the variable regions. Thus, the variant sequences present in an allele can be determined from the subset of probes which hybridize to that allele. Although, in general, each individual probe can hybridize to several alleles, each allele hybridizes to a unique subset of the probes.

The boundaries of the polymorphic regions within the HLA-B alleles are somewhat arbitrary and depend in part on the length chosen to define a region. A recommended definition of polymorphic (variable) regions of the second, third, and fourth exons of the HLA-B gene is shown below. These polymorphic regions are determined from a comparison, i.e., sequence alignment, of the DNA sequences of the HLA-B alleles. The sequences of the known HLA-B alleles are available from GenBank. Once the polymorphic regions have been defined, the sequence variants which occur within the polymorphic regions are obtained from the published HLA-B allele sequences. One of skill in the art will be able to design and use suitable probes to detect the sequence variant.. In particular, the references describing HLA Class II typing systems cited above provide guidance for the design and use of a suitable probe set.

TABLE 6

Variable Regions of the HLA-B Alleles

| Exon | Region | Codons |
|---|---|---|
| Exon 2 | A | 5 to 18 |
|  | B | 20 to 27 |
|  | C | 28 to 35 |
|  | D | 36 to 55 |
|  | E | 60 to 75 |
|  | F | 72 to 90 |
| Exon 3 | G | 2 to 10 |
|  | H | 9 to 20 |
|  | I | 21 to 30 |
|  | J | 50 to 58 |
|  | K | 60 to 64 |
|  | L | 63–70 |
|  | M | 70 to 80 |
|  | N | 80–84 |
|  | O | 84–95 |
| Exon 4 | P | 4 to 15 |
|  | Q | 50 to 60 |

For a given set of probes, the expected pattern of probe hybridization for each individual allele is easily obtained by comparing the published sequence of each allele with each probe sequence. Similarly, the expected pattern of probe hybridization for each of the possible heterozygous genotypes is obtained by combining the individual allele hybridization patterns. The genotype of an unknown sample is then determined by comparing the pattern of probe hybridization with the possible probe hybridization patterns. A computer program to generate the possible hybridization patterns and to perform the comparisons necessary to determine an unknown genotype is easily written.

It will be clear to one of skill in the art that sets of sequence-specific probes can be chosen which identify classes of alleles, rather than uniquely identify each allele. In some applications, identification of all alleles is not necessary. For example, the methods of the present invention can be used to detect allelic variants not distinguishable by serological methods. Because tissue typing for use in organ transplantation requires identification of only the serological types, it may be desirable to use a set of probes which distinguishes between the sets of alleles which correspond to each serological type, but does not distinguish between the alleles within each serological type. Use of such a set of probes can provide a significant reduction in the number of probes required.

Suitable assay formats for detecting hybrids formed between probes and target nucleic acid sequences in a sample are known in the art, and include the dot-blot and reverse dot-blot assay formats.

In a dot-blot format, amplified target DNA is immobilized on a solid support, such as a nylon membrane (se Sambrook et al., 1985, supra). The membrane-target complex is incubated with labeled probe under suitable hybridization conditions, unhybridized probe is removed by washing under suitably stringent conditions, and the membrane is monitored for the presence of bound probe.

An alternate format is a "reverse" dot-blot format, in which the amplified target DNA is labeled and the probes are immobilized on a solid support, such as a nylon membrane (see Saiki et al., 1989, Proc. Natl. Acad. Sci. USA 86:6230, and Erlich and Bugawan, 1989, supra, both incorporated herein by reference). The target DNA is typically labeled during amplification by the incorporation of labeled primers. The membrane-probe complex is incubated with the labeled sample under suitable hybridization conditions, unhybridized sample is removed by washing under suitably stringent conditions, and the filter is then monitored for the presence of bound target DNA.

Alternatively, the reverse dot-blot assay may be carried out using a solid support having a plurality of probe hybridization sites or wells. For example, a microwell plate is particularly useful in large scale clinical applications of the present methods. Probes can be immobilized to a microwell plate either by passive binding or by first binding the probes to bovine serum albumin (BSA), which adheres to microwell plates. Reverse dot-blot methods carried out in a microtiter plate are described in copending U.S. application Ser. No. 141,355, and U.S. Pat. No. 5,232,829, both incorporated herein by reference.

In a reverse dot-blot format, the target DNA is typically labeled during amplification by the incorporation of labeled primers. Primers can be labeled by incorporating a label detectable by spectroscopic, photochemical, biochemical, immunochemical, or chemical means. Useful labels include 32p, fluorescent dyes, electron-dense reagents, enzymes (as commonly used in ELISAS), biotin, or haptens and proteins for which antisera or monoclonal antibodies are available. Labeled primers of the invention can be synthesized and labeled using the techniques described above for synthesizing oligonucleotides. In a preferred embodiment of the invention, the primers are labeled with biotin. Following amplification using the labeled primers and hybridization with the immobilized probes, the amplified nucleic acid is detected by first binding the biotin to streptavidin-horseradish peroxidase (SA-HRP), which is then detected by carrying out a reaction in which the HRP catalyzes a color change of a chromogen (see Erlich and Bugawan, 1989, supra).

Genotyping at the HLA-B locus is useful for many different purposes. For example, the typing methods of the present invention can be used to discover new alleles. The presence of a new allele will result in the amplified product hybridizing to the set of sequence-specific probes in a novel pattern. The existence of a new allele can be confirmed by cloning and sequencing of the amplified product or by direct sequencing of the PCR products from the above amplification. The preferred primers of the present invention contain restriction enzyme cleavage sites at the 5' end, which facilitate cloning of the amplified product. Suitable sequencing methods are known in the art (Sambrook et al., 1985, supra).

The typing methods of the invention have valuable clinical applications. The Class I gene products of the major histocompatibility complex (MHC) are the major barrier for allogeneic tissue transplantation. Hence, the HLA-B genotyping system will be valuable in typing potential transplantation donors, where very precise HLA matching appears to be critical in minimizing risk of rejection or graft versus host disease. Another clinical use is identifying individuals with increased disease susceptibility.

Another application of the typing system of the invention is in identifying the source of a biological sample. DNA typing methods now play a significant role in the important area of individual identification, whether for solving crimes, as when the identity of a criminal or victim is established by linking an individual with evidence left at the scene of a crime, or for solving other issues of a non-criminal nature, as when biological material is used to determine the maternity or paternity of an individual.

The present invention also relates to kits, multicontainer units comprising useful components for practicing the present method. A useful kit can contain primers for PCR amplification of an HLA-B target region and SSO probes for identifying the HLA-B alleles. In some cases, the SSO probes may be fixed to an appropriate support membrane. Other optional components of the kit include, for example, an agent to catalyze the synthesis of primer extension products, the substrate nucleoside triphosphates, means used to label (for example, an avidin-enzyme conjugate and enzyme substrate and chromogen if the label is biotin), the appropriate buffers for PCR or hybridization reactions, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the an from reading the foregoing text and following examples.

EXAMPLE 1

Amplification of HLA-B Genomic DNA

A. Generic Amplifications

The following protocol is for the PCR amplification of all HLA-B alleles. Amplifications are carried out using between 100–500 ng of genomic DNA in 100µl reactions volumes. The primers, ET1148 (SEQ ID NO:3) and ET1147 (SEQ ID NO:5), are used to amplify the 1.6 kb fragment described above. Each primer is biotinylated for use in a reverse dot-blot detection method. Each reaction contains the folllowing regents:

50 pmoles of each primer,

100µM each dATP, dCTP, and dGTP,

200µM dUTP, 50 mM KCl, 10 mM Tris-HCl (pH 8.4), 1.5 mM $MgCl_2$, 5.0 units of Taq DNA polymerase*, and 15% Glycerol.

* manufactured and developed by Hoffmann-La Roche and marketed by Perkin Elmer, Norwalk, Conn.

Amplifications are carrier out in a TC9600 DNA thermal cycler (Perkin Elmer, Norwalk, Conn) using the following temperature profile:

| Initial Denature: | 95° C for 5 minutes; |
|---|---|
| 35 cycles: | denature at 95° C. for 30 seconds, anneal at 60° C. for 1 minute, and extend at 72° C. for 90 seconds; |
| Final Extension | 72° C. for 5 minutes. |

Amplification sometimes may yield a spurious product about 800 base pairs in length resulting from a low level of hybridization of the upstream primer to a second site downstream of the intended site. The presence of this artifactual product does not interfere with allele identification using the methods of the present invention.

B. Group-Specific Amplification

The following protocol is used to amplify specific subsets of the HLA-B alleles. A group-specific second amplification is used only as required to resolve probe binding pattern ambiguities. Amplifications are carried out essentially as described above for the generic amplifications, but using a group-specific upstream primer as described above.

Amplifications are carried out in a TC9600 DNA thermal cycler (Perkin Elmer, Norwalk, Conn.) using the following temperature profile:

| Initial Denature: | 95° C. for 5 minutes; |
|---|---|
| 35 cycles: | denature at 95° C. for 30 seconds, anneal at 55–65° C. for 30–60 seconds, and extend at 72° C. for 90 seconds; |
| Final Extension | 72° C. for 5 minute. |

EXAMPLE 2

Amplification of HLA-B from Human Cell Lines

This example describes the amplification of HLA-B alleles from human cell lines. Each of the cell lines had been previously characterized according to either genotype or serotype, or both. The cell lines tested are listed in Table 7, below, along with the genotype and/or serotype. In Table 7, "allele 1" and "allele 2" refer to the two alleles present in heterozygous cell lines. For homozygous cell fines, the single allele type or serotype is indicated under "allele 1".

TABLE 7

| | Cell Lines Typed | | | |
|---|---|---|---|---|
| | DNA Genotype | | Serotype | |
| Sample Name | Allele #1 | Allele #2 | Allele #1 | Allele #2 |
| 3232 | 5702 | 7801 | 57 | 78 |
| AMAL | 530011 | | 53 | |
| APA (Paau) | 1502 | 5502 | 55 | 75 |
| BM15 | | | 49 | |
| BM16 | | | 18 (6) | |
| BM21 | | | 41 | |
| BM92 | 5101 | | 51 | |
| CB68 | | | 62 | |
| COX | | | 08 | |
| DBB | | | 57 (4) | |
| E4181324 | | | 52 (4) | |
| GRC212 | 3505 | | 35 | 40 |
| H0301 | | | 14 | |
| JBUSH | | | 38 | |
| JHAF | | | 51 (4) | |
| JY | 0702 | | 7 | |
| KASO | 3701 | | 37 | |
| KRC0103 | 4801 | 3506 | 39 | 40 |
| LB | 4001 | | 60 | |
| LBUF = LBF | 1302 | | 13 | |
| LH | 2702 | | | |
| LKT-3 | 5401 | | 54 (6) | |
| LUY | | | 51 (4) | |
| LWAGS | | | 14 (6) | |
| LZL | 1502 | | 75 | |
| MG | 3701 | | 13 | 37 |
| OLGA | | | 62 | |
| OMW | | | 45 | |
| PITOUT | 4403 | | 44 | |
| PLH | 4701 | | | |
| RML | | | 51 | |
| RSH | | | 42 (6) | |
| SAVC | | | 7 | |
| SHJO | 5001 | | 42 | 50 |
| SWEIG 007 | 4002 | | 61 | |
| T7526 | 4601 | | 46 | |
| TISI | | | 35 (6) | |
| VEN | 5501 | | 18 | 55 |
| VOO | 5601 | | 56 | 8 |
| WT49 | 5801 | | | |
| YAR | | | 38 | |

Between 250 and 500 ng of genomic DNA from the each of the cell lines were amplified essentially as described in Example 1 using the primer pair ET1148 (SEQ ID NO 3) and ET1147 (SEQ ID NO:5). Amplified products were analyzed by gel electrophoresis and by hybridization with sequence-specific probes.

Amplification resulted in the generation from all the cell lines tested of a distinct band of the expected size when analyzed by gel electrophoresis. The results indicate that the primer pair ET1148 (SEQ ID NO3) and ET1147 (SEQ ID NO:5) efficiently amplified HLA-B nucleic acid from each of the cell types.

We claim:

1. A primer for the polymerase chain reaction amplification of HLA-B locus nucleic acid, wherein said primer consists of a subsequence of SEQ ID NO:2 comprising bases 5–21 of SEQ ID NO:2.

2. A primer for the polymerase chain reaction amplification of HLA-B nucleic acid, wherein said primer consist of a first nucleotide sequence which constitutes the 3' end of the primer, and a second sequence which constitutes the 5' end of said primer, wherein said first sequence consists of a primer of claim 1, and wherein said second sequence is between about 2 and about 10 nucleotides in length and contains a restriction enzyme cleavage site.

3. A primer of claim 2 which is selected from the group consisting of ET1147 (SEQ ID NO:5), and ET1130 (SEQ ID NO:6).

4. A kit for amplifying HLA-B nucleic acid, wherein said kit comprises a palmer of claim 1.

5. A kit for amplifying HLA-B nucleic acid, wherein said kit comprises a primer of claim 2.

6. A kit for amplifying HLA-B nucleic acid, wherein said kit comprises a primer of claim 3.

7. A method for amplifying a HLA-B nucleic acid, wherein said method comprises carrying out a polymerase chain reaction using a primer of claim 1.

8. A method for amplifying a HLA-B nucleic acid, wherein said method comprises carrying out a polymerase chain reaction using a primer of claim 2.

9. A method for amplifying a HLA-B nucleic acid, wherein said method comprises carrying out a polymerase chain reaction using a primer of claim 3.

10. A primer for the polymerase chain reaction amplification of HLA-B locus nucleic acid, wherein said primer is a subsequence of ET1074 (SEQ ID NO:7) comprising bases 5–24 of ET1074 (SEQ ID NO:7).

11. A primer for the polymerase chain reaction amplification of HLA-B locus nucleic acid, wherein said primer consists of a first nucleotide sequence which constitutes the 3' end of the primer, and a second sequence which constitutes the 5' end of said primer, wherein said first sequence consists of a primer of claim 10, and wherein said second sequence is between about 2 and about 10 nucleotides in length and contains a restriction enzyme cleavage site.

12. A kit for amplifying HLA-B nucleic acid, wherein said kit comprises a primer of claim 10.

13. A kit for amplifying HLA-B nucleic acid, wherein said kit comprises a primer of claim 11.

14. A method for amplifying a HLA-B nucleic acid, wherein said method comprises carrying out a polymerase chain reaction using a primer of claim 10.

15. A method for amplifying a HLA-B nucleic acid, wherein said method comprises carrying out a polymerase chain reaction using a primer of claim 11.

16. A primer for the polymerase chain reaction amplification of HLA-B nucleic acid, wherein said primer is a subsequence of an oligonucleotide that is ET1163 (SEQ ID NO:17), wherein said subsequence comprises bases 5 through the 3' terminal base of said oligonucleotide.

17. A primer for the polymerase chain reaction amplification of HLA-B nucleic acid, wherein said primer consists of a first nucleotide sequence which constitutes the 3' end of the primer, and a second sequence which constitutes the 5' end of said primer, wherein said first sequence consists of a primer of claim 16, and wherein said second sequence is between about 2 and about 10 nucleotides in length and contains a restriction enzyme cleavage site.

18. A kit for amplifying HLA-B nucleic acid, wherein said kit comprises a primer of claim 16.

19. A kit for amplifying HLA-B nucleic acid, wherein said kit comprises a primer of claim 17.

20. A method for amplifying a HLA-B nucleic acid, wherein said method comprises carrying out a polymerase chain reaction using a primer of claim 16.

21. A method for amplifying a HLA-B nucleic acid, wherein said method comprises carrying out a polymerase chain reaction using a primer of claim 17.

* * * * *

UNITED STATES PATENT AND TRADEMARK OFFICE
CERTIFICATE OF CORRECTION

PATENT NO. : 5,550,039
DATED : August 27, 1996
INVENTOR(S) : Elizabeth A. Trachtenberg It is certified that error appears in the above-indentified patent and that said Letters Patent is hereby corrected as shown below:

In column 23, Claim 2, line 2, please delete "consist" and insert therefor --consists--.

In column 23, Claim 4, line 2, please delete "palmer" and insert therefor --primer--.

Signed and Sealed this

Fourteenth Day of January, 1997

Attest:

BRUCE LEHMAN

Attesting Officer     Commissioner of Patents and Trademarks